(12) United States Patent
Siemons et al.

(10) Patent No.: US 7,002,469 B2
(45) Date of Patent: Feb. 21, 2006

(54) REMOTE DENTAL DISPLAY SYSTEM

(75) Inventors: Alexander H. Siemons, Sierra Madre, CA (US); Darren Saravis, Long Beach, CA (US)

(73) Assignee: Ormco Corporation, Orange, CA (US)

( * ) Notice: Subject to any disclaimer, the term of this patent is extended or adjusted under 35 U.S.C. 154(b) by 102 days.

(21) Appl. No.: 10/729,762

(22) Filed: Dec. 5, 2003

(65) Prior Publication Data
US 2005/0058962 A1    Mar. 17, 2005

Related U.S. Application Data

(60) Provisional application No. 60/431,119, filed on Dec. 5, 2002.

(51) Int. Cl.
| | |
|---|---|
| G08B 1/08 | (2006.01) |
| G08B 5/22 | (2006.01) |
| B60Q 1/00 | (2006.01) |
| G08C 19/00 | (2006.01) |
| H04N 7/18 | (2006.01) |

(52) U.S. Cl. ............ 340/539.12; 340/438; 340/286.07; 340/825.36; 340/825.69

(58) Field of Classification Search .......... 340/539.12, 340/438, 286.07, 825.36, 825.69, 573.1; 348/66–74
See application file for complete search history.

(56) References Cited

U.S. PATENT DOCUMENTS

| | | | | |
|---|---|---|---|---|
| 6,057,758 | A * | 5/2000 | Dempsey et al. | ...... 340/539.12 |
| 6,525,664 | B1 * | 2/2003 | Erland | ........................ 340/635 |
| 2003/0222109 | A1 * | 12/2003 | Weiss | ........................ 224/222 |
| 2003/0223455 | A1 * | 12/2003 | Rashdan | ..................... 370/466 |

* cited by examiner

Primary Examiner—Jeffery Hofsass
Assistant Examiner—Lam Pham
(74) Attorney, Agent, or Firm—Wood, Herron & Evans, L.L.P.

(57) ABSTRACT

A remote display unit is positioned to display remotely generated data without requiring a doctor to turn his or her head away from the object of the doctor's attention.

24 Claims, 4 Drawing Sheets

US 7,002,469 B2

REMOTE DENTAL DISPLAY SYSTEM

CROSS-REFERENCE TO RELATED APPLICATION

This application claims the benefit of the filing date of Provisional U.S. patent application Ser. No. 60/431,119 entitled "Remote Dental Display System" and filed on Dec. 5, 2002. The entire disclosure of that provisional U.S. patent application is incorporated into this application by reference.

FIELD OF THE INVENTION

The present invention relates to dental procedures, and more particularly, to the monitoring of equipment and conditions in a patient's oral cavity relating to teeth, gums and/or jawbone.

BACKGROUND OF THE INVENTION

Awareness of equipment and patient status facilitate efficient and otherwise successful dental procedures. To this end, such procedures routinely rely on a number of monitors and other fixed displays to relay pertinent data to a doctor. For instance, dental procedures conventionally implicate numerous such displays associated with any number of procedures ranging from root canals and bridgework, to tooth transplants. Economic and practical considerations continue to force doctors to expand his or her expertise and proficiency to include still other techniques and associated equipment.

More particularly, each dental procedure typically requires its own respective battery of supporting equipment. For example, equipment for an oral surgical procedure may include a hand drill coupled to a monitor or other display. The monitor may display a numerical torque readout that must be continuously monitored by a doctor. The same procedure may additionally involve irrigation equipment. The irrigation equipment may have its own display configured to present data relating to flow rate, as well as pump and reservoir status. Another exemplary procedure may involve an apex locator and/or a curing unit.

The competing space, wiring and functional requirements of such displays and their associated equipment often precludes positioning the displays within a single field of vision. Consequently, a doctor must continuously turn away from one display to view another or the patient. This action causes the doctor to frequently interrupt his or her view of, for instance, a patient's oral cavity, increasing the potential for inefficiency and patient injury. Such disruption further contributes to doctor fatigue and physical stresses attributable to neck and back contortion.

Consequently, and for in part the above delineated reasons, there exists a need for an improved manner of monitoring dental equipment displays.

SUMMARY OF THE INVENTION

The present invention enhances dental procedures by improving doctor access to pertinent data. A remote display unit consistent with the principles of the present invention minimizes problems associated with the prior art by enabling a doctor to selectively view the data apart from the dental unit from which the data originates. The remote display unit thus communicates the data to the doctor in a manner largely liberated from bulky and/or inopportunely positioned dental units. As such, the doctor may position the remote display unit within his field of view, thus avoiding having to turn his head away from the patient or other object of his attention.

In one respect, an embodiment of the present invention capitalizes on the processing power of more robust, conventional dental base units to remotely display dental parameters gleaned from the base units in a manner that requires relatively little processing hardware. The smaller hardware requirements allow for small, easily positioned and unobtrusive remote display units that attach in the doctor's field of vision. Moreover, the remote display unit is compatible with conventional dental base units and thus does not require the purchase of additional equipment. An embodiment of the present invention may further require less power than comparable displays that are part of the dental base unit that generates the dental data.

More particularly, the remote display unit displays data communicated from one or more remote dental base units. Exemplary dental base units include oral drills, syringes, apex locators, irrigation/air flow regulators, filler dispensers, pulse monitoring equipment and/or conceivably any device having application in a dental procedure. As such, exemplary dental base units having particular application within certain embodiments of the present invention may include devices that must be continuously or periodically monitored by a doctor during dental procedure. In any case, the connections between the remote display unit and the base unit(s) may be cable or wireless. Further, the remote display unit of one embodiment may be integral with or otherwise attached to a dental base unit or support structure, such as a chair, watchband or lamp.

A remote display system consistent with the invention may communicate information pertinent to the operation of one or more dental units to a controller in communication with a display of the remote display unit. The controller may format the embedded data of the received signal for the display. The display of the remote display system communicates pertinent data to the doctor through text, audible cues, graphs, colors, shapes, lights and/or some combination thereof. Exemplary data includes: apex and temperature readings, torque settings, as well as hand piece speed and pressure levels.

A doctor may customize the remote display unit to communicate one or more parameters involved in a given procedure. For instance, multiple dental data parameters may be simultaneously displayed to convey the synergistic relationship present between complementary parameters. In one application, for example, torque and motor speed and file depth readings may provide insight into the comprehensive operation and relative position of a hand drill. Further, dispenser status may be displayed in conjunction with data from an apex finder to provide an oral surgeon with a more comprehensive perspective. Where desired, the doctor may change the type of dental data displayed and/or the manner in which it is displayed. Alternatively, the type of dental data displayed may automatically transition according to a preprogrammed sequence.

By virtue of the foregoing there is provided an improved display system that addresses shortcomings of prior art systems. These and other objects and advantages of the present invention shall be made apparent in the accompanying drawings and the description thereof.

BRIEF DESCRIPTION OF THE DRAWINGS

The accompanying drawings, which are incorporated in and constitute a part of this specification, illustrate an embodiment of the invention and, together with a general description of the invention given above, and the detailed description of the embodiment given below, serves to explain the principles of the invention.

DETAILED DESCRIPTION OF THE PREFERRED EMBODIMENTS

Figure 1:
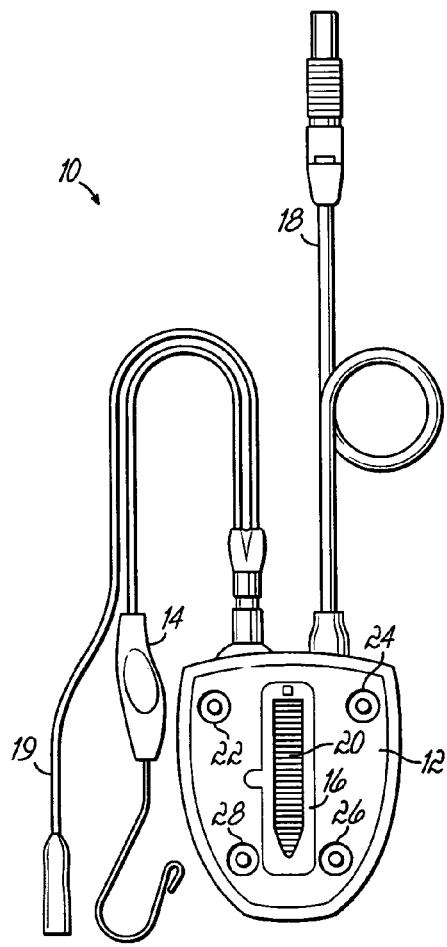
FIG. 1 shows a remote display unit that is consistent with the principles of the present invention.
Figure 2:
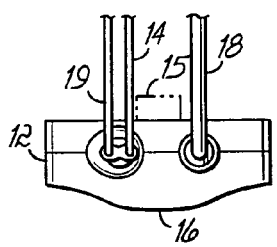
FIG. 2 shows a top view of the remote display unit of FIG. 1.

Referring generally to FIGS. 1 and 2, there is shown a remote display unit 10 configured to present data within the view of a doctor during a dental procedure. The remote display unit 10 comprises an enclosure 12 configured to attach to a patient, a doctor or an object positioned within the same field of view as the attention of the doctor. To this end, the remote display unit 10 includes one or more fasteners 15 for attachment purposes.

As will be appreciated by one of skill in the art after a full reading of this specification, the size and shape of an enclosure 12 that is consistent with the principles of the present invention may vary per application requirements. For example, the size of the enclosure 12 illustrated in FIGS. 1 and 2 is less than about an inch in length and a quarter of an inch in thickness. However, dimensions may be altered as needed to enable a doctor to concurrently monitor dental parameters as they view the object of a dental procedure.

As discussed below in greater detail, the remote display unit 10 includes a controller configured to receive and format signals for presentation at a display 16. In an embodiment where the controller is contained within the enclosure 12, the controller receives signals from one or more remote dental units via input cable 18.

A suitable display 16 in communication with the controller may support text, graphs, numerical readouts, projected lights, shapes, colors and video, among other display formats. For instance, the display 16 of the exemplary remote display unit 10 of FIG. 1 includes a series of light emitting diodes (LED's) 20. The LED's 20 may sequentially illuminate in a manner to indicate, for instance, the proximity of a probe to an apex. As seen best in FIG. 2, the enclosure 12 may bulge to provide better views of the display 16.

Figure 3:
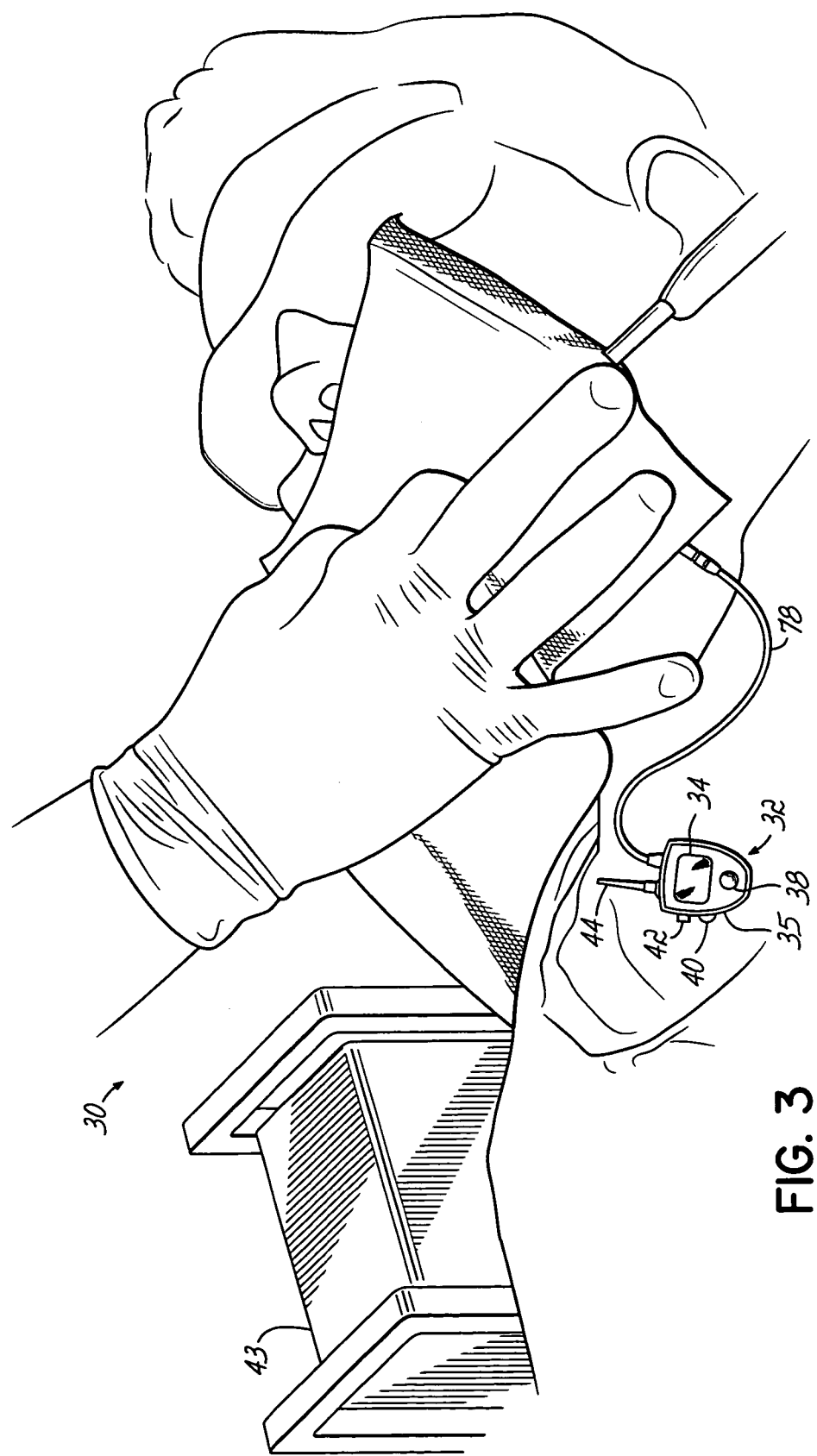
FIG. 3 shows another remote display unit that is consistent with the principles of the present invention in use during a dental procedure.

In the embodiment shown in FIG. 3, the exemplary display 34 of the remote display unit 32 incorporates liquid crystal display (LCD) technology. LCD's generally include nematic liquid crystals contained within a transparent, conductive medium. When electrified, the crystals transmit and polarize light in such a manner as the structure of the crystals alters to produce a desired image on the display 34, such as a numerical readout or table. One skilled in the art will appreciate that a comparable display of another remote display unit that is consistent with the principles of the present invention may support digital video images.

In any case, the type and quantity of dental data displayed may selectively vary according to doctor input and/or a preprogrammed sequence. For instance, the remote display unit 32 in use in FIG. 3 receives dental parameters from, among other base units, a thermal drainage suction pump 43.

As with the embodiment shown in FIGS. 1 and 2, the remote display unit 32 of FIG. 3 includes a fastener (not shown). While not limited to such, an exemplary fastener may include a hook, epoxy, a clip, or clasp, as shown in FIG. 3. Other suitable fasteners may include hook and loop fasteners, a screw, a strap, a wire or any device known to hold an object in a desired position.

While one skilled in the art will appreciate that the processes and hardware of an embodiment of the present invention may transfer into other medical endeavors, monitored parameters, or data, for purposes of this specification include both variable parameters reflecting the condition of an oral cavity undergoing a dental procedure and variable parameters related to equipment used during a dental procedure. For instance, such parameters may relate to a parameter selected from the group consisting of: an instrument location, an instrument orientation, a power status, a direction of rotation, a motor speed, a torque level, a power level, a magnification setting, a reservoir capacity, a flow rate, a pressure reading, a temperature reading, a time hack, a display setting and any combination thereof. Exemplary oral cavity conditions include the location of a root canal and the relative position of a probe within the root canal, as well as conditions relating to teeth, gums and/or bone.

More specific examples of equipment related parameters include drill speed and torque, irrigating fluid flow rate and temperature, among other data. For that matter, a doctor or other user for purposes of this specification typically includes an endodontist, an orthodontist, a dentist, a medical doctor, a technician, a transplant specialist, a surgeon or other specialist desiring the display of pertinent data within his or her field of vision.

Displayed parameters may be updated continuously and automatically throughout a dental procedure using the remote display unit 32. Those parameter selections viewed via the display 34 may furthermore be customized or otherwise selectable by a doctor at the onset of and throughout an application. That is, a doctor may tailor the display 34 to meet particular application requirements and personal preferences. For instance, a dental application may call for the display of dental data generated by a hand drill and an apex locator, but not a scalar. As such, a display 34 associated with the scalar may be disabled upon initialization of the display system.

Such settings may be accomplished via a thumb wheel/scroll button 38, dial 40, toggle switch 42, microphone, keypad or other interface mechanism that is in communication with the controller. As such, the controller may be further configured to receive signals from a voice transducer. Such a configuration may allow a doctor to setup a display sequence using voice recognition software. Other settings may be hardwired or preprogrammed into the controller as per manufacturer specifications or user interface "skins," such as background color, downloaded via the Internet or other network.

While the exemplary controller in communication with the display 34 may comprise a sophisticated computer system or network, a suitable controller for purposes of another embodiment that is consistent with the principles of the underlying invention may include any device having electronics configured to receive and transmit signals. One of skill in the art should appreciate that a controller for purposes of this specification may furthermore comprise a plurality of separate circuits, each configured to receive and relate data to another controller or one of a plurality of displays and/or remote display units.

While either or both the controller and display 34 may be integral with the enclosure 35 of the remote display unit 32, other embodiments consistent with the invention may position the controller remotely from the enclosure. Furthermore, the controller may communicate signals to the display 34 of the remote display unit 32 using wireless connections, such as radio and/or infrared frequency waves, as well as laser beam applications.

It should be appreciated by one of skill in the art that embodiments of the present invention may accommodate and actually enhance existing dental hardware setups. The controller, enclosure 35 and associated hardware/software of the remote display unit 32 may be purchased to augment, and not merely supplant, existing base systems. Such a feature enables doctors to enjoy advantages associated with embodiments of the present invention without having to discard prior investment and established preferences associated with existing base dental equipment.

Figure 4:
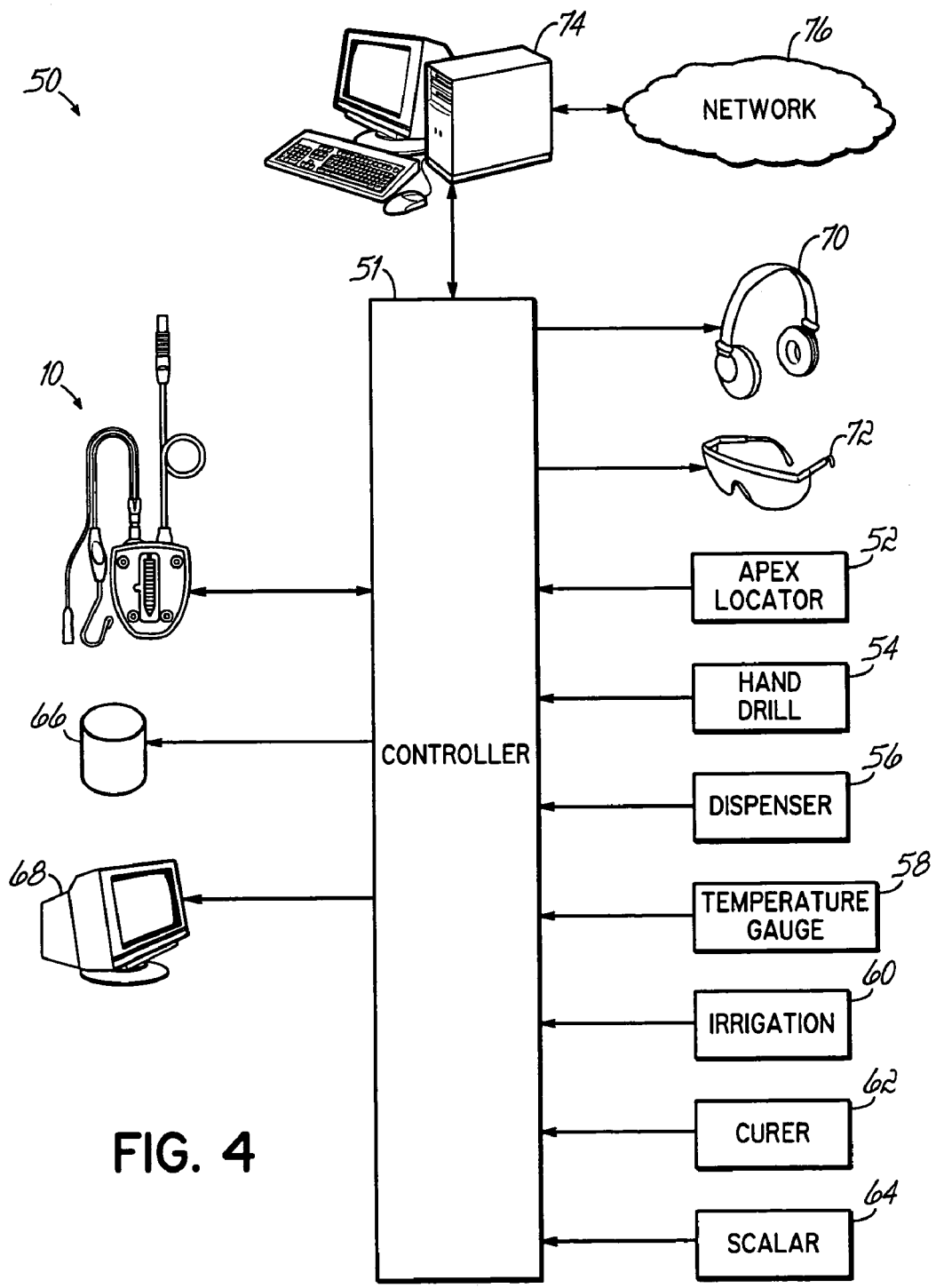
FIG. 4 shows a display system that is consistent with the principles of the present invention and that includes the remote display unit of FIG. 1.

FIG. 4 shows a display system 50 that is consistent with the principles of the present invention. The system includes a remote display unit 10 coupled to a controller 51. The controller 51 is typically integral with the unit 10 and may comprise multiple, separate processors. The controller 51 additionally communicates directly or indirectly with a plurality of dental base units 52–64. The dental base units 52–64 may include dental modules and their associated conventional displays, as well as other equipment useful in dental applications. For example, exemplary devices may include an apex locator 52, a surgical drill 54, a filler dispenser 56 and an air/irrigation flow device 60, in addition to respective display monitors. Still other devices may include a curing unit 62 and a scalar device 64. Connections to the controller 51 from the respective devices 52–64 may be wireless, such as through the use of radio waves.

One skilled in the art should recognize that the dental base units 52–64 shown in FIG. 4 are included for exemplary purposes only, and may be substituted with other tools as required for a particular application, dental or otherwise. As such, suitable dental base units may comprise any equipment configured to sample or detect a parameter and communicate a signal indicative of the measured parameter. Devices having application with embodiments of the present invention may further be networked with other devices as desired. For,instance, the controller 51 of the system 50 shown in FIG. 4 communicates with a memory 66 from which settings may be retrieved and parameters pertaining to a dental procedure may be stored. The controller 51 additionally communicates with an additional monitor 68 that may display the same or different dental parameters for reference by the doctor or others observing the dental procedure. Still another connection shown in FIG. 4 allows communication between the controller 51 and a server 74 associated with a network 76.

In operation, a doctor may utilize one or more of the dental base units 52–64 while viewing dental parameters at the remote display unit 10. That is, dental parameters detected at one or more of the respective dental base units 52–64 may be communicated to the controller 51 of the remote display unit 10. For instance, the apex locator 52 may periodically or continuously transmit a signal to the controller 51. Of note, a suitable controller 51 in one embodiment may be integral with one or more of the dental base units 52–64. Such a configuration may, for instance, allow for peer-to-peer type communications. Data embedded within the signal may convey a distance or location of a probe relative to the apex of a patient's root canal. Another device 58 may simultaneously transmit a second signal to the controller 51 relating a measured temperature reading.

The controller 51 may convert the format of the arriving signals to one that is compatible with the remote display unit 10 as needed. The controller 51 may update the display 16 of dental parameters as new signals from one or more of the dental base units 52–64 arrive at the controller 51. Thus, the doctor is made continuously aware of data pertaining to the patient, equipment and ongoing procedure. According to doctor or manufacturer preferences, some aspects of a display 16 may appear only at the onset of an application. The display of other parameters may automatically initiate in response to detection of a preset condition. For example, warning message may flash on a screen display of an exemplary remote display unit when a drill bit exceeds a predetermined depth in an oral cavity.

In some applications, the remote display unit 10 presents a combination, or product of different dental parameters. For instance, a green LED 24 flashing at the onset of a procedure may indicate that both an irrigation dispenser and reservoir are in useable condition. Displayed data from one dental base unit may compliment that from another to provide a synergistic impression to a doctor. For example, the display 16 may include a visual indicator relating to both drill torque and position. Thus, the configurable display 16 may communicate information to sophisticated users in an easily digestible and insightful manner. Displays of other embodiments may be tailored so as to only communicate dental parameters relating to equipment status, irrespective of patient-related information. Such equipment variable parameters may include detected torque of a drill 54, flow rate of an irrigation system 60, and/or operating status of an apex locator 52.

It should be noted that suitable displays 16 included within the remote display unit 10 may comprise any known presentation device fashioned to communicate visual and/or audio data. As such, the display 16 may accommodate a photograph, hologram or streaming video of images, to include the oral cavity of the patient. Moreover, an exemplary remote display unit may attach to or include a pair of goggles 72, a visor or other eyewear adorned by a doctor. Another remote display system may include headphones 70 or other broadcast audio systems configured to sound audio warnings or other cues initiated by the controller 51.

Those skilled in the art will recognize that the exemplary hardware environments illustrated in FIGS. 1–4 are not intended to limit the present invention. Indeed, those skilled in the art will recognize that other alternative hardware and/or software environments may be used without departing from the scope of the invention.

Figure 5:
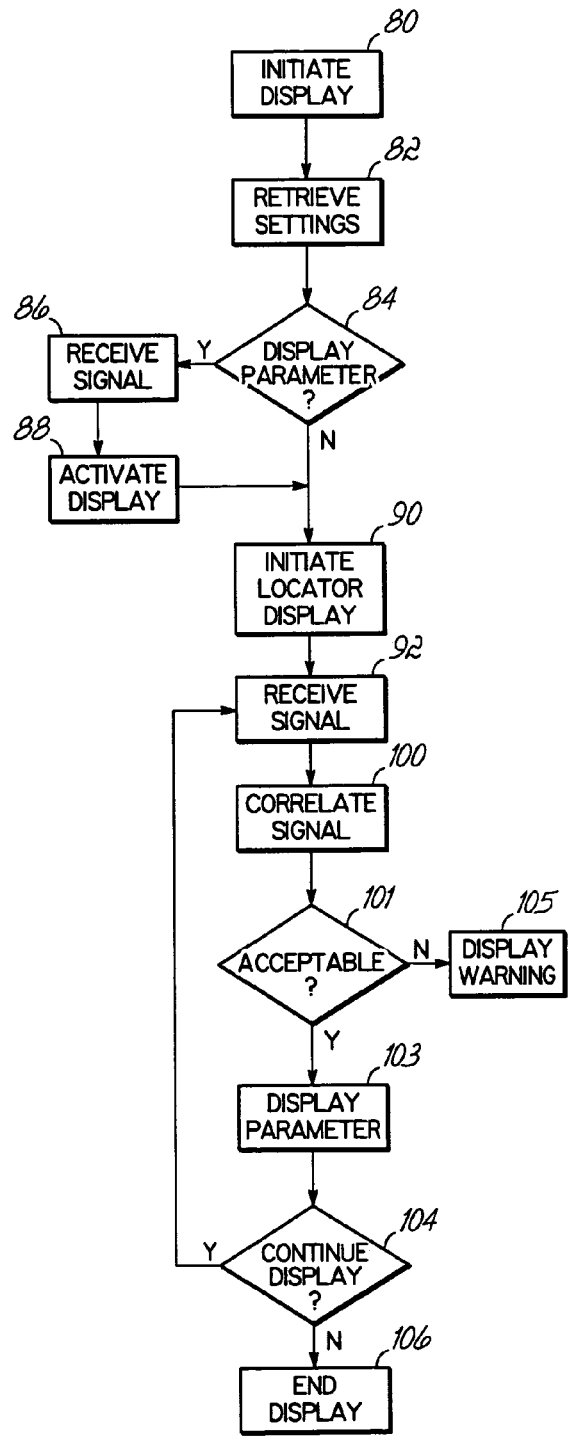
FIG. 5 is a flowchart outlining method steps in accordance with the principles of the present invention and suited for execution within the system of FIG. 4.

FIG. 5 is a flowchart having sequenced method steps suited for execution within the dental system 50 of FIG. 4. Prior to initiating a display sequence at block 80, a doctor may attach the remote display unit 10 to an object in line with her view of an oral cavity or important monitor. An exemplary fastener 15 used to attach the unit 10 may include a clip configured for insertion into a patient chair or a microscope. Another fastener may include an aperture in the housing configured to receive a corresponding, securing structure. Such a structure may include a clip or an instrument handle. For instance, a remote display unit may slip over the handle of an apex locator probe so as to be viewable by the doctor as they manipulate the probe.

At block 80 of the flowchart, the controller 51 may initiate a light sequence or other display routine intended to convey to a doctor an operational status of the remote display unit 10 and/or dental base units 52–64. For instance, a LED 24 of the remote dental unit 10 may flash rapidly in order to communicate to the doctor that its display 16 is properly initiating.

The controller 51 may retrieve relevant settings from memory 66 or user input received at the remote display unit 10 at block 82. Such settings may be preset into the controller 51 and/or be adjustable by the doctor along any step of a dental procedure. Settings may be accomplished via a touch pad, voice recognition software, or another interface on or remote from the enclosure 12. Settings configurable via the remote display unit 10 may regard the type and sequence of dental parameters to be displayed. For instance, some settings may call for certain parameters to be displayed only in response to a particular condition being realized. One such condition may include detection of a critical pressure reading for a hand tool. For instance, a display 16 may flash in response to the detected torque of a hand drill 54 exceeding a threshold limit.

The controller 51 may initiate the display 16 at the remote display unit 10 at block 84 according to the settings retrieved at block 82. That is, the controller 51 may sample the retrieved settings at block 84 to determine if a given dental parameter should be displayed. For instance, the controller 51 may evaluate the settings retrieved at block 82 to determine if the "powered" status of an apex locator 52 should be displayed at the remote display unit 10. Where so configured, the controller 51 may receive a signal at block 86 from the apex locator 52. The signal may convey the operational status of the apex locator module 52. Where the signal indicates full power, for instance, the controller 51 may initiate activation of a green LED 24. Of note, while presentation of a green light 24 may suit the display purposes of one embodiment of the present invention, other embodiments may employ blinking lights, changing shapes and/or colors, text, as well as an auditory signal.

At block 90, the controller 51 may sample the settings retrieved at block 82 to determine if positional data regarding the apex locator 18 should be displayed. If so configured, then the controller 51 may receive and evaluate a signal from the apex locator module 52 beginning at block 92. The signal may convey dental data pertaining to a distance traveled by the apex locator probe relative to a fixed point within the patient's tooth. The signal as received at block 92 may be correlated to a table or otherwise processed at block 100 as necessary to generate a control signal.

In one instance, a suitable control signal may be formatted to initiate a display 16 indicative of the locator distance at block 103. Where appropriate, the control signal may alternatively initiate a warning display 16 at block 105. For instance, a digital readout may flash when the probe of the apex locator exceeds a preset, minimum distance from the apex. As such, the evaluation processes begun at block 100 may include an initial screening for the warning condition at block 101. The controller 51 may then transmit the control signal to the display 16 at either block 103 or 105, as appropriate.

At block 103, the control signal may effectively activate LED's 20 of the display 16 as appropriate to communicate data conveyed in the signal from the apex locator module 52 at block 92. In the environment 30 of FIG. 3, the control signal may alternatively initiate electron flow through an LCD configured to present a numerical readout of the apex probe location. That is, a numerical readout may communicate the distance of the probe from the apex. As such, the doctor may monitor the locator information as they simultaneously conduct the procedure. Where so desired at block 104 of FIG. 5, the dental data presented via the display 16 at block 103 may be updated as subsequent signals arrive from the apex locator module 52. Significantly, the doctor does not have to turn away from the patient to monitor the changing location of the probe. Thus, the flow of the procedure remains uninterrupted, contributing to greater efficiency and accuracy.

Figure 6:
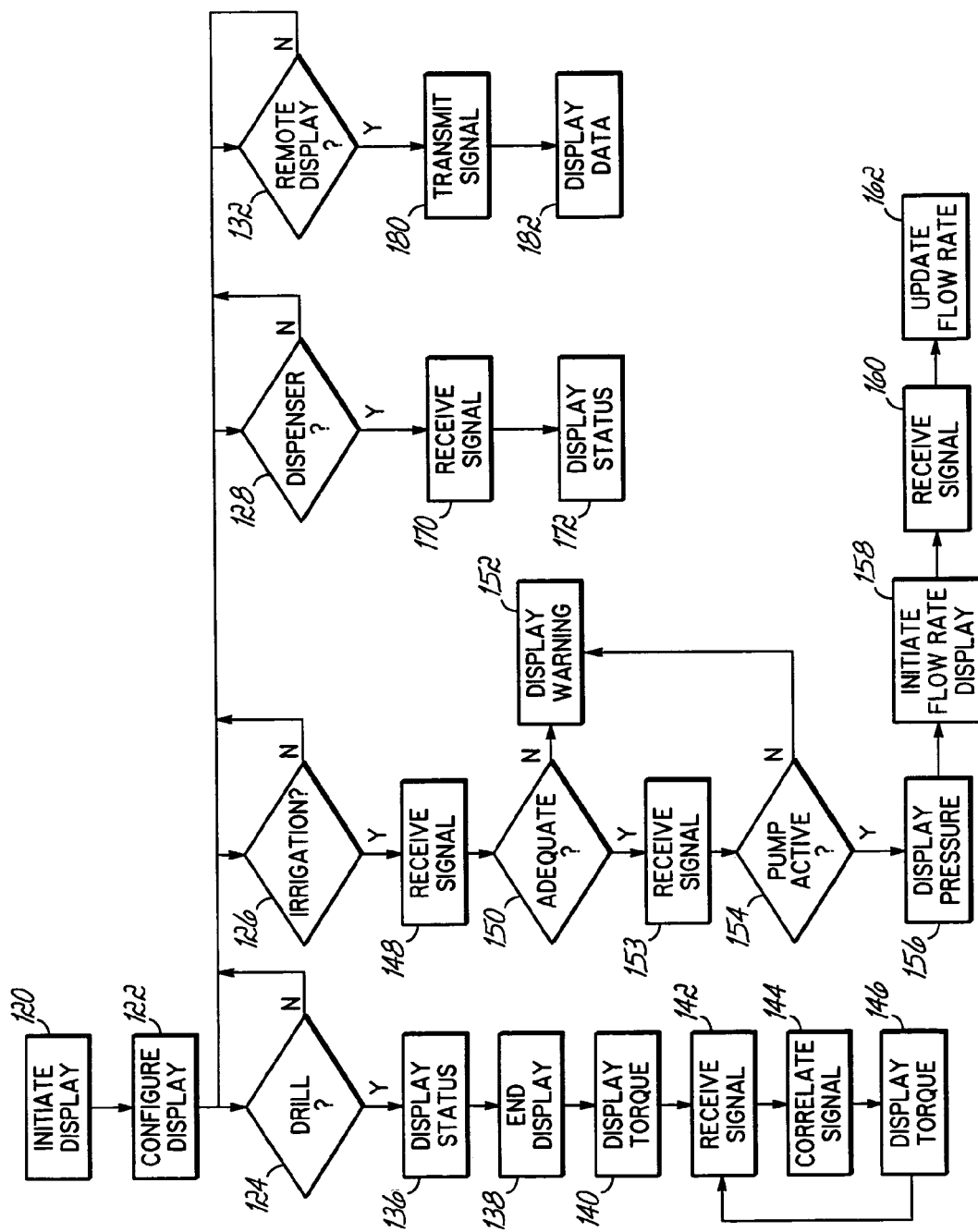
FIG. 6 is a flowchart outlining method steps of another embodiment in accordance with the principles of the present invention and also being suited for execution within the remote display system of FIG. 4.

FIG. 6 is a flowchart having method steps that are also suitable for implementation within the hardware environments of FIGS. 1–4, and which highlight synergistic display features that are possible with embodiments of the present invention. At block 120, a controller 51 as described herein may cue the display 16 of the system 10. That is, lights or other indicators of the display 16 may activate to communicate the status of initialization processes to a doctor. The controller 51 may then prompt the doctor for display settings, while accessing any stored settings at block 122.

Exemplary settings may include the programmatic designation of which dental parameters the doctor wishes to display. For instance, the doctor may elect to have data pertaining to a drill 54, an irrigation module 60 and a filler dispenser 56 at step 128 presented within the same display 16. Aspects of the selected and displayed data may communicate a comprehensive and synergistic perspective to the doctor. Such perspective may translate into unique insights and increased awareness regarding a procedure. Thus, while dental parameters may be separately viewed by a doctor as desired, the unique display features of the present invention may allow monitoring of different parameters, conjunctively.

In operation, the controller 51 may receive a status signal from a hand drill base unit 54 at block 136. The status signal may be transmitted to the controller 51 in response to a determination at block 124 that dental parameters relating to the hand drill device 54 are desired. The status signal sent from the hand drill base unit 54 may communicate to the controller 51, for instance, whether the drill is powered.

Accordingly, the controller 51 may initiate a display 16 of such status information at block 136. In one embodiment, the display 16 may be automatically terminated at block 138 by the controller 51 in response to the expiration of a preset increment of time. For instance, it may be desirable for the status display 16 at block 136 to last for about two seconds. Such a configuration may be desirable where a doctor only wishes to be made initially aware of the drill's availability or power status.

Where so configured, the controller 51 may then automatically initiate a display 16 of drill torque at block 140. That is, the controller 51 may retrieve settings from within the system 50 that instruct the controller 51 to automatically display a torque parameter related from the hand drill 54. Thus, the doctor does not have to manually initialize the display 16. Initialization processes may precede reception of a signal from the hand drill device 54 at block 142. The controller 51 may extract and correlate information conveyed within the signal at block 144 to produce a control signal formatted so as to affect the display 16 at block 146.

Should the settings of block 122 indicate that irrigation information is additionally desired, the controller 51 may receive a signal from the irrigation module 60 at block 148. At block 150, the controller 51 may determine from the signal whether the water capacity in a reservoir of the irrigation module 60 exceeds some minimum threshold level. If not, then the controller 51 may initiate a display 16 of a red warning light 26 at block 152. The warning light 26 may communicate to the doctor a potentially problematic scenario stemming from the detected shortage of fluid in the reservoir.

Should the binary evaluation conducted by the controller 51 at block 150 alternatively determine that the reservoir has an adequate amount of fluid, than the controller 51 may next receive signal 153 to determine whether dental parameter relating to a pump component of the irrigation module 60 is ready/powered at block 154. Should the pump be underpowered or have inadequate pressure as determined by the controller 51 at block 154, then the warning light 26 may activate at block 152. Alternatively, the display 16 may present a pressure reading to the doctor at block 156 in response to the detection of adequate pressure levels. As such, the controller 51 may evaluate the status of the pump only after the reservoir status has first been established. Thus, a doctor may infer from the presentation of pump data that the status of the irrigation equipment is operational. In this manner, two parameters may combine within the display 16 to form a single dental data point. As such, the display 16 of one embodiment may account for a combination of dental data in an easily digestible format.

Where desired, the display 16 of yet another dental parameter relating to the irrigation equipment may be automatically initiated at block 158. The controller 51 may initiate the display 16 of a flow rate associated with the irrigation module 60, which may be updated via signal information from the irrigation module 60 at block 160. Where so configured, the same signal from the irrigation module 60 may convey all of the information evaluated at blocks 150, 154 and 158. The controller 51 may then update the flow rate display at block 162 prior to re-sequencing through the method steps at block 126. Thus, an embodiment of the present invention continuously monitors and updates dental data in a feedback loop.

The method steps of the flowchart of FIG. 6 may further accommodate the display of dental parameters relating to equipment configured to dispense filler material. The display of such data may be initiated at block 128. Such a display may involve receiving a signal from a filler dispenser module 56 at block 170. The controller 51 may then display a level or other indicator relating to the capacity of the filled dispenser 56 at block 172. As such, a doctor may simultaneously view multiple, related types of dental parameters in such a manner that does not require a turn of the doctor's head.

In use, embodiments consistent with the principles of the present invention capitalize on the easily positioned nature of the remote display unit 10. Namely, by virtue of being positioned in the view of the doctor, the unit 10 may already be proximate the oral cavity. Wireless or cabled leads 18 and 19 from the remote display unit 10 couple to detectors configured to measure dental parameters. These dental parameters are thus routed and displayed to the doctor at the remote display unit 10 in a manner that does not obstruct a view of the oral cavity.

While the present invention has been illustrated by a description of various embodiments and while these embodiments have been described in considerable detail, it is not the intention of the applicants to restrict or in any way limit the scope of the appended claims to such detail. For example, user input received at a remote display unit, in addition or alternatively to reconfiguring displayed parameters, may initiate generation of a remote control signal configured to affect operation of a dental base unit. For instance, a remote control signal communicated from a remote display unit in response to a doctor's manipulation of a thumbwheel may switch off power to a scalar. Additional advantages and modifications will readily appear to those skilled in the art. For instance, while the exemplary method step sequences shown in FIGS. 5 and 6 may have particular utility in certain contexts, it should be understood that the order and content of such steps may be rearranged, omitted, augmented and/or modified to suit different system requirements.

Moreover, one skilled in the art should recognize that other embodiments of the present invention accommodate any number of display scenarios suited to application specifications and doctor preferences. For instance, while the principles of the present invention lend themselves advantageously to dentistry, or any practice concerning an oral cavity of a patient, embodiments of the invention are equally applicable to other medical and surgical endeavors outside of dentistry. Thus, the invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. A method for communicating dental data to a user comprising:
providing a remote display unit including an enclosure attached to a fastener and a display for communicating dental data to the user such that the user concurrently views the dental data and an object of a dental procedure; and
fastening the enclosure in proximity of the object within view of the user to communicate the dental data to the user.

2. The method of claim 1, further comprising generating the dental data at a dental base unit remote from the remote display unit.

3. The method of claim 1, further comprising receiving at the remote display unit a control signal conveying the dental data.

4. The method of claim 3, wherein receiving the control signal further includes receiving a wireless transmission.

5. The method of claim 1, further comprising communicating the dental data from a dental base unit to the remote display unit.

6. The method of claim 1, further comprising selectively communicating the dental data to the user via the remote display unit.

7. The method of claim 1, further communicating a remote control signal configured to affect operation of a dental base unit from the remote display unit to the dental base unit.

8. The method of claim 3, wherein receiving the signal at the remote display unit further comprises receiving the signal from a base unit configured to measure a parameter selected from the group consisting of at least one of: an instrument location, an instrument orientation, a power status, a direction of rotation, a motor speed, a torque level, a power level, a magnification setting, a reservoir capacity, a flow rate, a pressure reading, a temperature reading, a time hack and a display setting.

9. The method of claim 1, further comprising altering the dental data communicated via the display in response to at least one of received user input and an occurrence of a preset condition.

10. The method of claim 1, wherein communicating the dental data to the user further includes at least one of initiating the display and generating an audio cue in response to a preset condition.

11. The method of claim 1, wherein communicating the dental data to the user further includes communicating dental data comprising a plurality of dental parameters.

12. The method of claim 1, wherein communicating the dental data to the user further includes communicating dental data comprising a product derived from a plurality of dental parameters.

13. The method of claim 1, further comprising updating the dental data.

14. A remote display unit comprising:
an enclosure having a fastener for attachment proximate to an object of a dental procedure;
a display coupled to the enclosure, the display configured to communicate dental data to the user such that the user concurrently views the dental data and the object of the dental procedure; and
a controller in communication with the display configured to receive a control signal that conveys the dental data from a dental base unit having an associated display remote from the enclosure, wherein the controller is further configured to adjust the display to communicate the dental data to the user from the position.

15. The remote display unit of claim 14, wherein the dental data includes a parameter selected from the group consisting of at least one of: an instrument location, an instrument orientation, power status, magnification power, a power status, a direction of rotation, a motor speed, a torque level, a power level, a reservoir capacity, a flow rate, a pressure reading, a temperature reading, a time reading, a patient condition and a display setting.

16. The remote display unit of claim 14, wherein transmission of the control signal to the controller is wireless.

17. The remote display unit of claim 14, wherein the controller effectively simultaneously receives the dental data from a plurality of dental base units.

18. The remote display unit of claim 14, wherein the controller initiates disabling at least a portion of the remote display.

19. The remote display unit of claim 14, wherein the controller communicates the dental data by conjunctively processing multiple dental parameters.

20. The remote display unit of claim 14, wherein the display includes a presentation device selected from the group consisting of at least one of: a liquid crystal display, a television, a ray tube, a computer monitor, an eyepiece, eye wear, a light emitting diode and a laser projection device.

21. The remote display unit of claim 14, wherein the display is adjusted in response to at least one of user input and an occurrence of a preset condition.

22. The remote display unit of claim 14, wherein the dental data is communicated in a format selected from the group consisting of at least one of: text, a graph, a color scheme, video, a photograph, a numerical readout, a symbol, a shape scheme and a light.

23. The remote display unit of claim 14, further comprising a circuit for generating an audio signal.

24. A remote dental display system comprising:
a dental unit for generating dental data, wherein the dental unit includes an associated display;
an enclosure having a fastener for attachment proximate to an object of a dental procedure;
a remote display coupled to the enclosure, the display configured to communicate dental data to the user such that the user concurrently views the dental data and the object of the dental procedure; and
a controller in communication with the display configured to receive a signal that conveys the dental data from the dental unit, wherein the controller is further configured to adjust the display to communicate the dental data to the observer from the position.

* * * * *

UNITED STATES PATENT AND TRADEMARK OFFICE
CERTIFICATE OF CORRECTION

PATENT NO. : 7,002,469 B2 Page 1 of 1
APPLICATION NO. : 10/729762
DATED : February 21, 2006
INVENTOR(S) : Alexander H. Siemons and Darren Saravis It is certified that error appears in the above-identified patent and that said Letters Patent is hereby corrected as shown below:

Column 1
line 21, change "facilitate" to --facilitates--.

Column 3
line 3, change "serves" to --serve--.

Column 5
line 50, change "For,instance," to --For instance,--.

Column 6
line 28, change "compliment" to --complement--.

Column 8
line 62, change "affect" to --effect--.

Column 10
line 1, change "affect" to --effect--.
lines 24-25, change "applicant's" to --applicants'--.
line 52, change "affect" to --effect--.

Column 11
line 30, delete "power status".

Signed and Sealed this

Twenty-second Day of August, 2006

JON W. DUDAS
*Director of the United States Patent and Trademark Office*